United States Patent [19]

Loescher

[11] Patent Number: 5,722,394
[45] Date of Patent: Mar. 3, 1998

[54] MANUAL RESUSCITATOR PRESSURE MONITOR VALVE

[75] Inventor: Thomas C. Loescher, Encinitas, Calif.

[73] Assignee: Hudson Respiratory Care Inc., Temecula, Calif.

[21] Appl. No.: 779,773

[22] Filed: Jan. 7, 1997

[51] Int. Cl.⁶ ..................................... A62B 7/04
[52] U.S. Cl. ................ 128/205.24; 128/203.11; 128/205.13
[58] Field of Search ............ 128/205.24, 202.28, 128/203.11, 203.24, 205.13, 207.12, 207.16, 204.18

[56] References Cited

U.S. PATENT DOCUMENTS

| | | | |
|---|---|---|---|
| 4,239,038 | 12/1980 | Holmel | 128/205.13 |
| 4,622,964 | 11/1986 | Flynn | 128/205.13 |
| 4,774,941 | 10/1988 | Cook | 128/205.24 |
| 5,109,840 | 5/1992 | Daleiden | 128/205.24 |

FOREIGN PATENT DOCUMENTS

| | | | |
|---|---|---|---|
| 798660 | 11/1968 | Canada | 128/205.24 |
| 910065 | 11/1962 | United Kingdom | 128/205.13 |

Primary Examiner—Vincent Millin
Assistant Examiner—V. Srivastava
Attorney, Agent, or Firm—Jerry R. Seiler, Esq.

[57] ABSTRACT

A manual resuscitation valve assembly having a duckbill valve and a valve housing with an open concentric cavity includes a one-way valve exposed to said duckbill valve and extending into said cavity for monitoring peak inspiratory pressure.

13 Claims, 2 Drawing Sheets

MANUAL RESUSCITATOR PRESSURE MONITOR VALVE

BACKGROUND OF THE INVENTION

Manual resuscitators for delivering gas to a patient or person are well known in the art. Such apparatus include a non-rebreathing valve assembly, a ventilation bag, a gas inlet and reservoir valve assembly and usually an oxygen reservoir. The non-rebreathing valve assembly is secured to a gas supply mask for delivering gas to the patient or person to be resuscitated by compressing or squeezing the ventilation bag. A duckbill valve is typically used as the non-rebreathing valve, and gas is delivered via the mask which is placed on the patient's face over the mouth and nose. Manual resuscitators are often manufactured in different sizes to be used on patients of different age categories, and are commonly available in adult, child, infant, and neonate sizes. When resuscitating neonates, infants and small children, it is very desirable to monitor peak inspiratory pressure in order to avoid high inspiratory pressure which could cause injury to the patient. Although most manual resuscitation apparatus includes a safety valve for venting gas above a preset pressure, if the pressure relief cap or valve locking device has not been removed or released prior to use, the pressure relief valve will be inoperable and patient injury may occur. Thus, the ability to monitor peak inspiratory pressure during ventilation of the patient is extremely desirable, and is most critical when the patient is a small child, infant or neonate in which even relatively small high pressure ventilation could cause rupture of the delicate lung tissue. It is also desirable to monitor peak inspiratory pressure during manual ventilation of infants and neonates who have received continuous ventilation in order to maintain consistency of the pressure with that which the patient has been receiving. Thus, the desirability of incorporating a pressure monitor port in a manual resuscitation apparatus will be evident to those skilled in the art.

A prior art manual resuscitation apparatus is illustrated in FIG. 1, and includes a non-rebreathing valve housing A provided with a pressure monitoring pipe B having a pressure monitoring port C. The pressure monitoring port of the prior art device illustrated extends well beyond the upper surface of the valve housing thereby often interfering with convenient handling and use of the device during the manual resuscitation. Moreover, the pipe is susceptible to be broken off or damaged. The prior art pressure port shown also must be closed or sealed, for example requiring a cap D, to prevent gas from venting to the atmosphere when the bag is squeezed if a manometer or other pressure monitoring device is not secured to the port. Other prior art devices have a pressure monitoring port on the side of the valve which location also interferes with handling convenience and use. It is to the elimination of the aforesaid prior art problems that the present invention is directed.

SUMMARY OF THE INVENTION

The apparatus of the present invention is an improved resuscitation valve assembly and housing having a one-way valve for monitoring peak inspiratory pressure during use of the resuscitation apparatus. The valve is positioned so that it is conveniently accessible for being attached to a pressure monitoring apparatus, and does not interfere with the operator administering manual resuscitation. Moreover, the location of the pressure monitoring port and valve are substantially protected from damage by the valve housing. These as well as other advantages and features will be evident from the following detailed description.

DETAILED DESCRIPION OF THE PREFERRED EMBODIMENT

Figure 1:
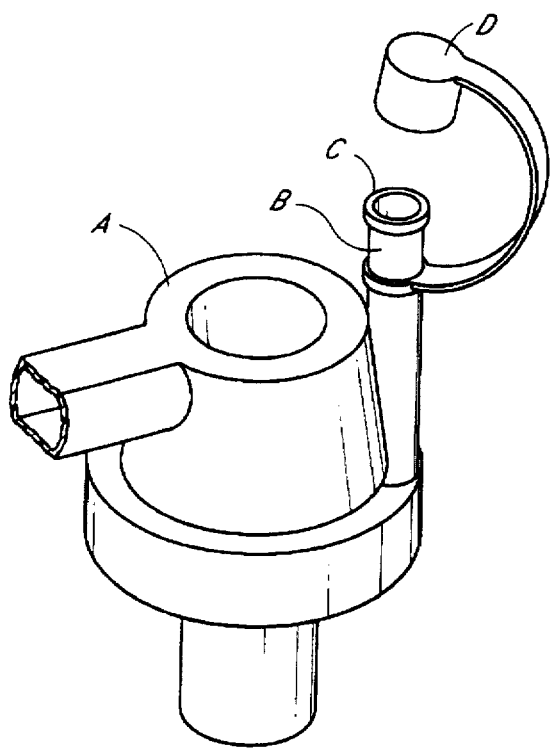
FIG. 1 shows a prior art device.
Figure 3:
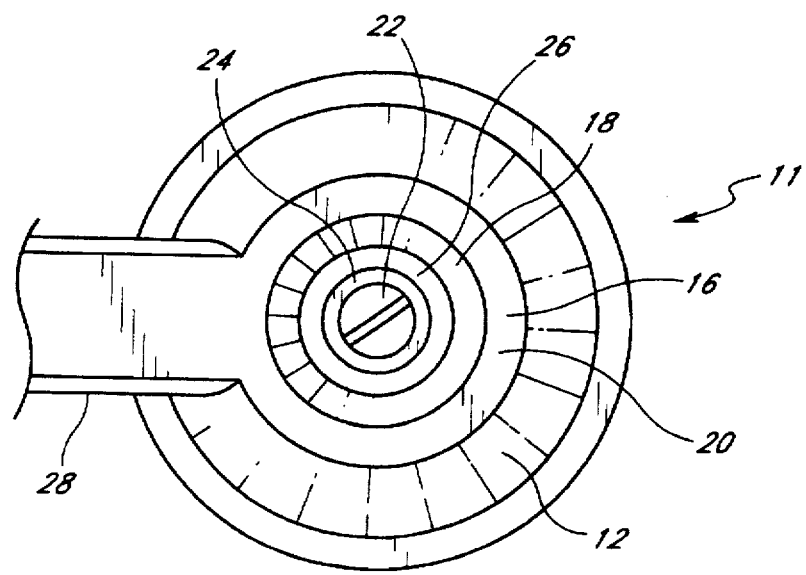
FIG. 3 is a top plan view of the valve housing shown in FIG. 2.
Figure 2:
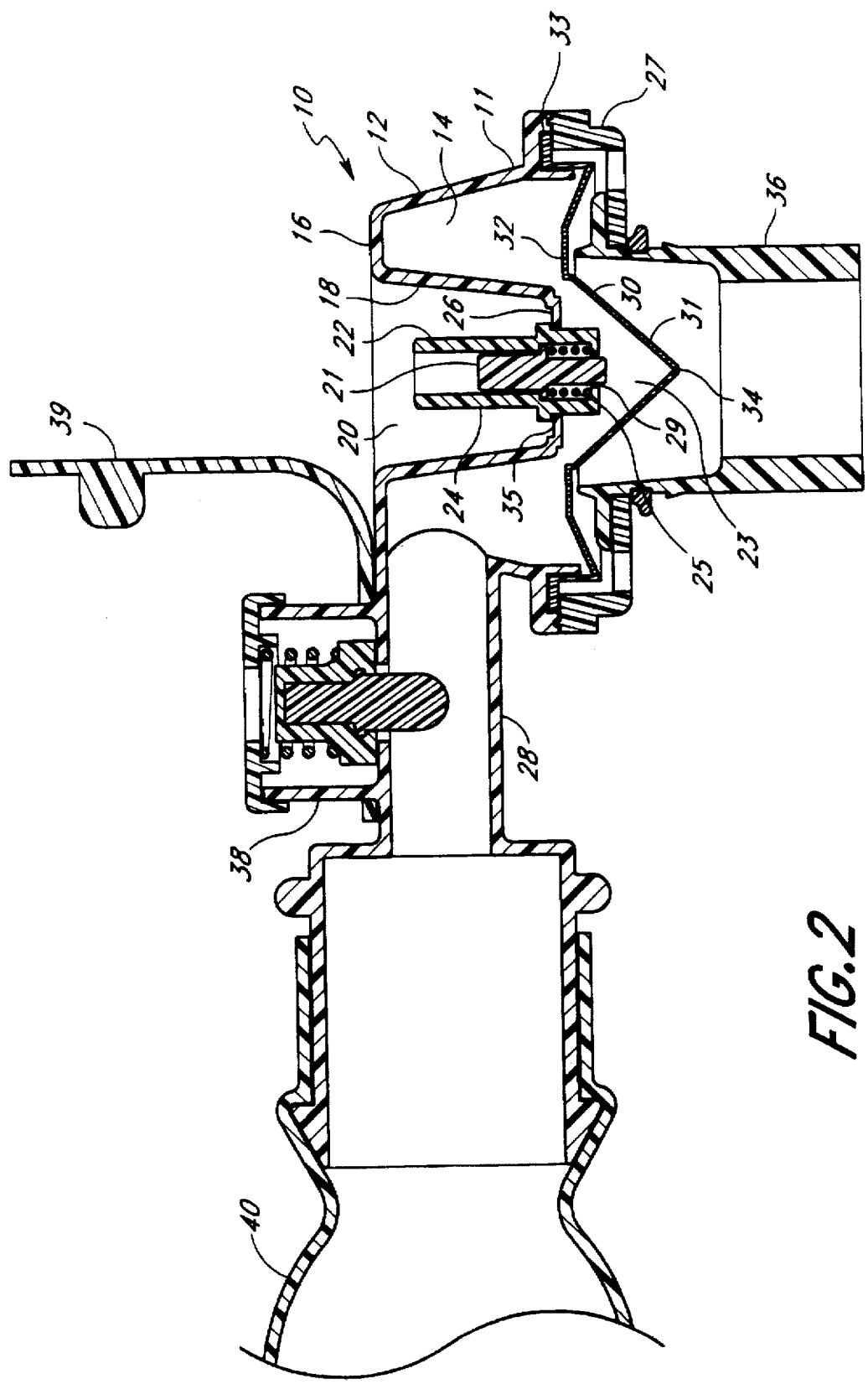
FIG. 2 is a side sectional elevation of the improved manual resuscitation valve assembly of the present invention.

In FIG. 2 the improved valve assembly of the present invention is illustrated in side sectional elevation and a top view of the valve housing is shown in FIG. 3. The valve assembly 10 includes a valve housing 11 having an outer wall 12 and an inner wall 18 which surround and define an interior gas chamber 14 which is substantially annular conforming to the shape between the outer and inner walls 12 and 18, respectively. A downstream or bottom housing 27, also annular in shape is secured to the underside of the valve housing 11, and an outlet fitting 36 is secured to the downstream housing. A complete manual resuscitation bag apparatus includes a patient mask (not shown) attached to the outlet fitting. The valve assembly includes a duckbill diaphragm valve 30 which is flexible and generally circular and having a duckbill valve portion 31 and a diaphragm portion 32. The duckbill diaphragm valve is secured along its outer peripheral edge 33 between valve housing 11 and downstream housing 27. A conduit 28 extends between a flexible ventilator bag 40 partially shown in FIG. 2 and the valve housing 11 providing a passageway for inspiratory gas forced from the squeezed ventilator bag to the annular gas chamber 14. The pressure of the inspiratory gas from the ventilator bag forces the duckbill valve port 34 open and the inspiratory gas passes through outlet fitting 36 to the patient via a patient resuscitation mask.

As shown in FIGS. 2 and 3, the outer and inner walls 12 and 18 are slanted somewhat from vertical toward a common top wall 16 to form a generally frustoconical valve housing wall structure, also defining the shape of the interior gas chamber 14. Although the shape of the specific valve housing embodiment shown is frustoconical, it should be understood that the invention is not limited to such a shape. For example, the valve housing may be substantially cylindrical whereby the inner and outer valve housing walls extend more parallel rather than slanted as shown. The interior valve housing wall 18 defines a cavity 20. The cavity is open at the upper end, the circular cavity opening defined by annular top wall 16. A bottom wall 26 at the base of the cavity is provided with an orifice 35 in which is secured one-way valve 22. The one-way valve comprises a an upstanding outer wall 24 to which tubing for a manometer or other pressure monitoring device may be secured. The one-way valve illustrated includes a spring 25 and a valve stopper 21 which is urged upwardly by the spring to maintain the valve normally closed. To measure or monitor the pressure, a suitable connector is inserted into one-way valve 22 depressing the valve stopper 21. Pressure at the peak of the inspiratory cycle, commonly referred to as peak inspiratory pressure, is monitored as the inspiratory gas from squeezed ventilator bag 40 flowing from the gas chamber 14 to duckbill valve port 34 passes through passageway 23. The gas is delivered to the patient through outlet fitting 36. This pressure differential is sensed or monitored by a suitable pressure monitoring device and will be observed as the peak inspiratory pressure. The valve shown may also be provided with means for adjusting the bias of the spring, whereby the pressure at which the valve opens may be selected and changed. Such means comprises a threaded component for adjusting the compression and bias of the spring, or other equivalent means. Other equivalent one-way or check valve structures may be substituted for the specific components and construction of the one-way valve shown so long as such valves are located within cavity 20 and secured at an orifice 35 along the bottom wall 26 of the cavity for monitoring and determining the inspiratory pressure of the gas delivered to the patient as the ventilator bag is squeezed. The valves are self-closing to substantially prevent leaking or venting of inspiratory gas from the gas chamber through the valve. The valve does not affect the operation of the duckbill valve nor the delivery of gas to the patient, and functions only to allow determination and monitoring of peak inspiratory pressure during manual resuscitation.

Although the previously described one-way valve shown in FIG. 2 is preferred, an alternative embodiment incorporates a one-way valve, normally closed and having a biased valve stopper, but which allows positive gas pressure in the inspiratory gas chamber above the duckbill valve port 34 to be monitored. The alternative valve is positioned the same as shown in FIGS. 2 and 3. Such a valve remains closed until the pressure within the gas chamber caused by squeezing the ventilator bag overcomes the one-way valve bias force. Preferably, the threshold pressure for opening the valve is below the pressure required to open the pressure relief valve 38, and well below a pressure which could cause injury to the patient. Once the bias for closing the valve is overcome, the valve opens sufficiently to allow inspiratory gas pressure to be monitored using a manometer or other suitable pressure monitoring device as previously described. The valve may include means for adjusting the biasing spring tension to provide selection and change of the gas pressure within the inspiratory gas chamber required to open the valve as previously described.

The manual resuscitation valve assembly illustrated in FIG. 2 also includes a pressure relief valve 38 having a valve stopper which can be selectively used for closing the pressure relief valve. Other features and components of such manual resuscitators as disclosed in Steven P. McPherson, Respiratory Therapy Equipment, 193, 194 (3d Ed. 1985) and incorporated herein by reference may be used in a complete manual resuscitation bag assembly provided with the one-way pressure monitoring valve of the present invention.

What is claimed is:

1. A manual resuscitation valve assembly comprising:
   a valve housing having a generally circular outer wall and a circular inner wall said walls defining an annular inspiratory gas chamber therebetween, and an open cavity concentric with and defined by said circular inner wall, a bottom wall at the base of said cavity, and an orifice in the center of said bottom wall,
   a duckbill valve for directing inspiratory gas from said inspiratory gas chamber to a patient, said duckbill valve being substantially coaxial with the center of said bottom wall, and
   a one-way valve secured in said orifice, said valve extending into said cavity for attaching a pressure monitor for monitoring inspiratory gas pressure.

2. The valve assembly of claim 1 wherein said inner wall and said outer wall are joined along a substantially planar annular top wall and wherein the distance of the inner wall from said bottom wall to said top wall is greater than the distance said one-way valve extends into said cavity.

3. The valve assembly of claim 2 wherein said valve housing is cylindrical or frustoconical.

4. The valve assembly of claim 1 wherein said one-way valve prevents gas from passing to atmosphere from said inspiratory gas chamber.

5. A manual resuscitator comprising a ventilation bag, a resuscitation valve assembly of claim 1, and a conduit extending between said bag and said valve housing for directing gas into said inspiratory gas chamber when said bag is squeezed, and a pressure relief valve secured on said conduit.

6. A manual resuscitator comprising a ventilation bag, a resuscitation valve assembly of claim 2, and a conduit extending between said bag and said valve housing for directing gas into said inspiratory gas chamber when said bag is squeezed, and a pressure relief valve secured on said conduit.

7. A manual resuscitator comprising a ventilation bag, a resuscitation valve assembly of claim 4, and a conduit extending between said bag and said valve housing for directing gas into said inspiratory gas chamber when said bag is squeezed, and a pressure relief valve secured on said conduit.

8. The valve assembly of claim 1 wherein said one-way valve includes a biased valve stopper for closing said valve until sufficient pressure in said inspiratory gas chamber overcomes the bias.

9. The valve assembly of claim 8 including adjustable biasing means for biasing said valve stopper.

10. A manual resuscitator comprising a ventilation bag, a resuscitation valve assembly of claim 8, and a conduit extending between said bag and said valve housing for directing gas into said inspiratory gas chamber when said bag is squeezed, and a pressure relief valve secured on said conduit.

11. A manual resuscitator comprising a ventilation bag, a resuscitation valve assembly of claim 9, and a conduit extending between said bag and said valve housing for directing gas into said inspiratory gas chamber when said bag is squeezed, and a pressure relief valve secured on said conduit.

12. The manual resuscitator of claim 10 wherein said valve stopper opens at a pressure below the pressure required to open said pressure relief valve.

13. The manual resuscitator of claim 10 wherein said biased valve stopper is adjustable to provide selection of the pressure required to open said one-way valve.

* * * * *